(12) United States Patent
White

(10) Patent No.: US 11,957,544 B1
(45) Date of Patent: Apr. 16, 2024

(54) MOTORIZED EAR-CLEANING DEVICE

(71) Applicant: Michael White, Brampton (CA)

(72) Inventor: Michael White, Brampton (CA)

( * ) Notice: Subject to any disclaimer, the term of this patent is extended or adjusted under 35 U.S.C. 154(b) by 164 days.

(21) Appl. No.: 17/516,799

(22) Filed: Nov. 2, 2021

(51) Int. Cl.
*A61F 11/00* (2022.01)
*A61M 3/02* (2006.01)

(52) U.S. Cl.
CPC .................................. *A61F 11/006* (2013.01)

(58) Field of Classification Search
CPC ............... A61F 11/006; A61M 3/0279; A61M 2210/0618; A61M 2210/0662; A46B 13/02
See application file for complete search history.

(56) References Cited

U.S. PATENT DOCUMENTS

| D296,005 | S | 5/1988 | Alkire | |
|---|---|---|---|---|
| 4,901,391 | A | 2/1990 | Athalye | |
| D368,373 | S | 4/1996 | Shimatsu | |
| 5,632,756 | A | 5/1997 | Kruglick | |
| 6,067,714 | A * | 5/2000 | Taylor | B26B 19/148 30/29.5 |
| 6,187,021 | B1 * | 2/2001 | Wim | A61F 11/006 606/162 |
| 7,500,981 | B1 | 3/2009 | Jubrail | |
| 9,549,854 | B1 * | 1/2017 | Crespo | A61F 11/006 |
| 2007/0009368 | A1 | 1/2007 | Yang | |
| 2016/0256327 | A1 * | 9/2016 | Kim | A61F 15/001 |
| 2016/0302973 | A1 * | 10/2016 | Kraitzer | A61M 31/00 |

* cited by examiner

*Primary Examiner* — Anh T Dang

(57) ABSTRACT

The motorized ear-cleaning device is a tool. The motorized ear-cleaning device is a therapeutic device. The motorized ear-cleaning device is adapted for use with the ear of a patient. The motorized ear-cleaning device cleans the ear. The motorized ear-cleaning device comprises a working element, a handle structure, and drive circuit. The working element attaches to the handle structure. The drive circuit mounts in the drive structure. The drive circuit rotates the working element. The rotation of the working element rubs against the ear. The working element generates a friction used to clean the ear.

5 Claims, 3 Drawing Sheets

MOTORIZED EAR-CLEANING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical devices including devices for the treatment of ears, more specifically, an ear cleaner. (A61F11/006)

SUMMARY OF INVENTION

The motorized ear-cleaning device is a tool. The motorized ear-cleaning device is a therapeutic device. The motorized ear-cleaning device is adapted for use with the ear of a patient. The motorized ear-cleaning device cleans the ear. The motorized ear-cleaning device comprises a working element, a handle structure, and drive circuit. The working element attaches to the handle structure. The drive circuit mounts in the drive structure. The drive circuit rotates the working element. The rotation of the working element rubs against the ear. The working element generates a friction used to clean the ear.

These together with additional objects, features and advantages of the motorized ear-cleaning device will be readily apparent to those of ordinary skill in the art upon reading the following detailed description of the presently preferred, but nonetheless illustrative, embodiments when taken in conjunction with the accompanying drawings.

In this respect, before explaining the current embodiments of the motorized ear-cleaning device in detail, it is to be understood that the motorized ear-cleaning device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the motorized ear-cleaning device.

It is therefore important that the claims be regarded as including such equivalent construction insofar as they do not depart from the spirit and scope of the motorized ear-cleaning device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
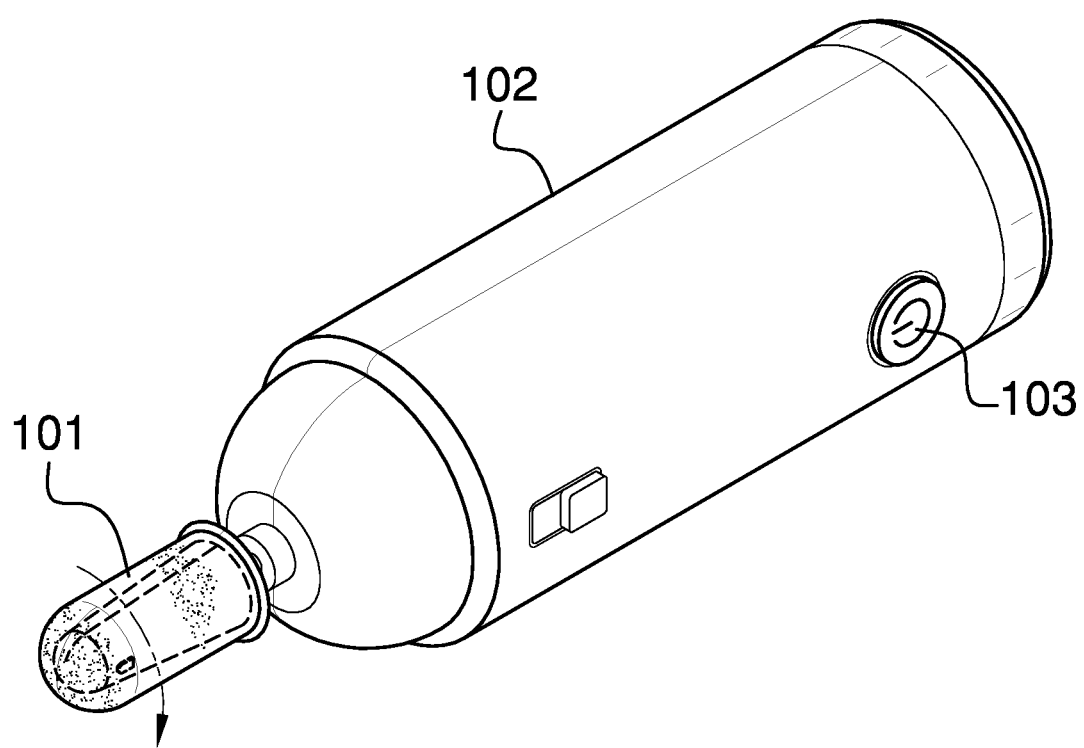
FIG. 1 is a perspective view of an embodiment of the disclosure.
Figure 2:
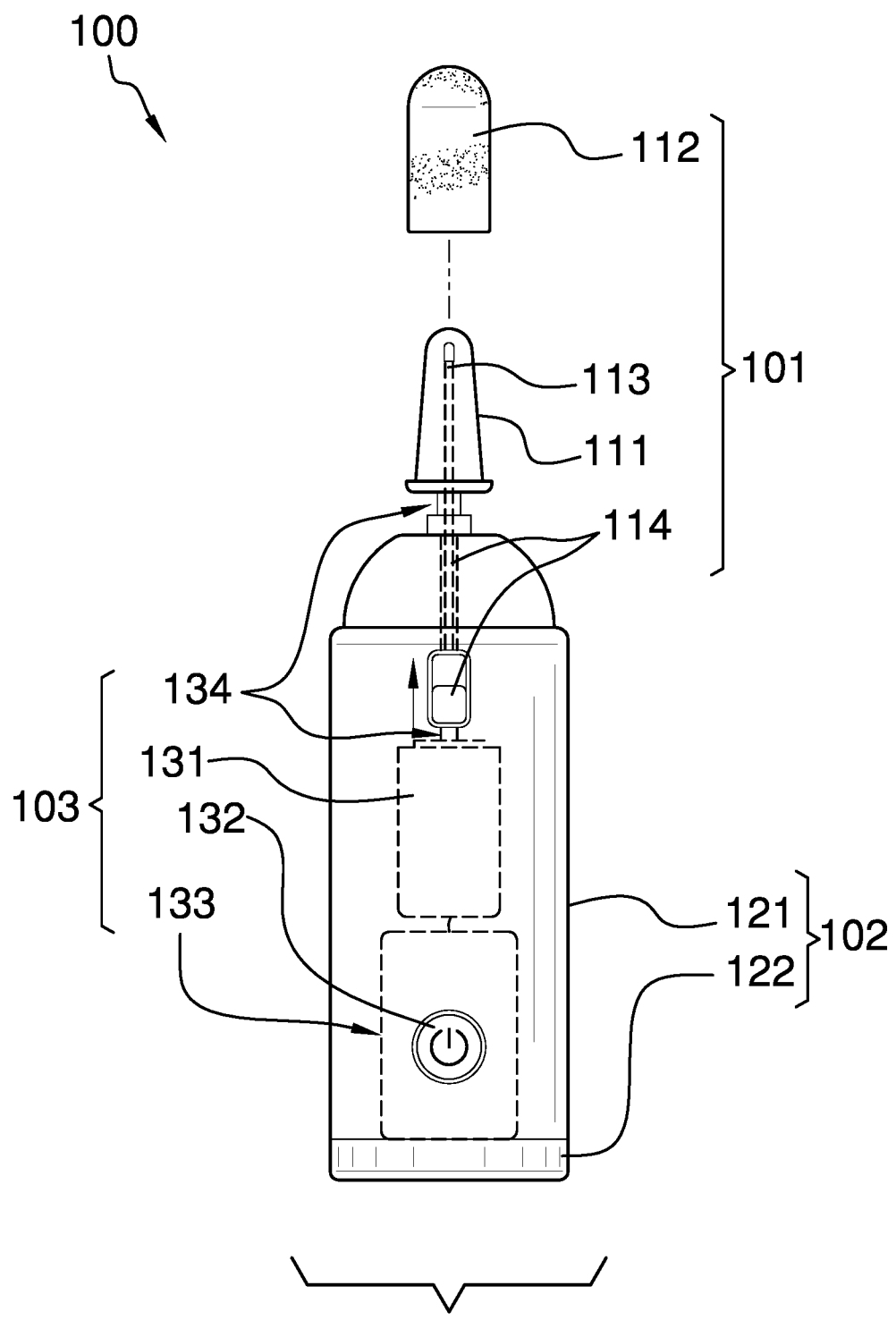
FIG. 2 is a detail view of an embodiment of the disclosure.
Figure 3:
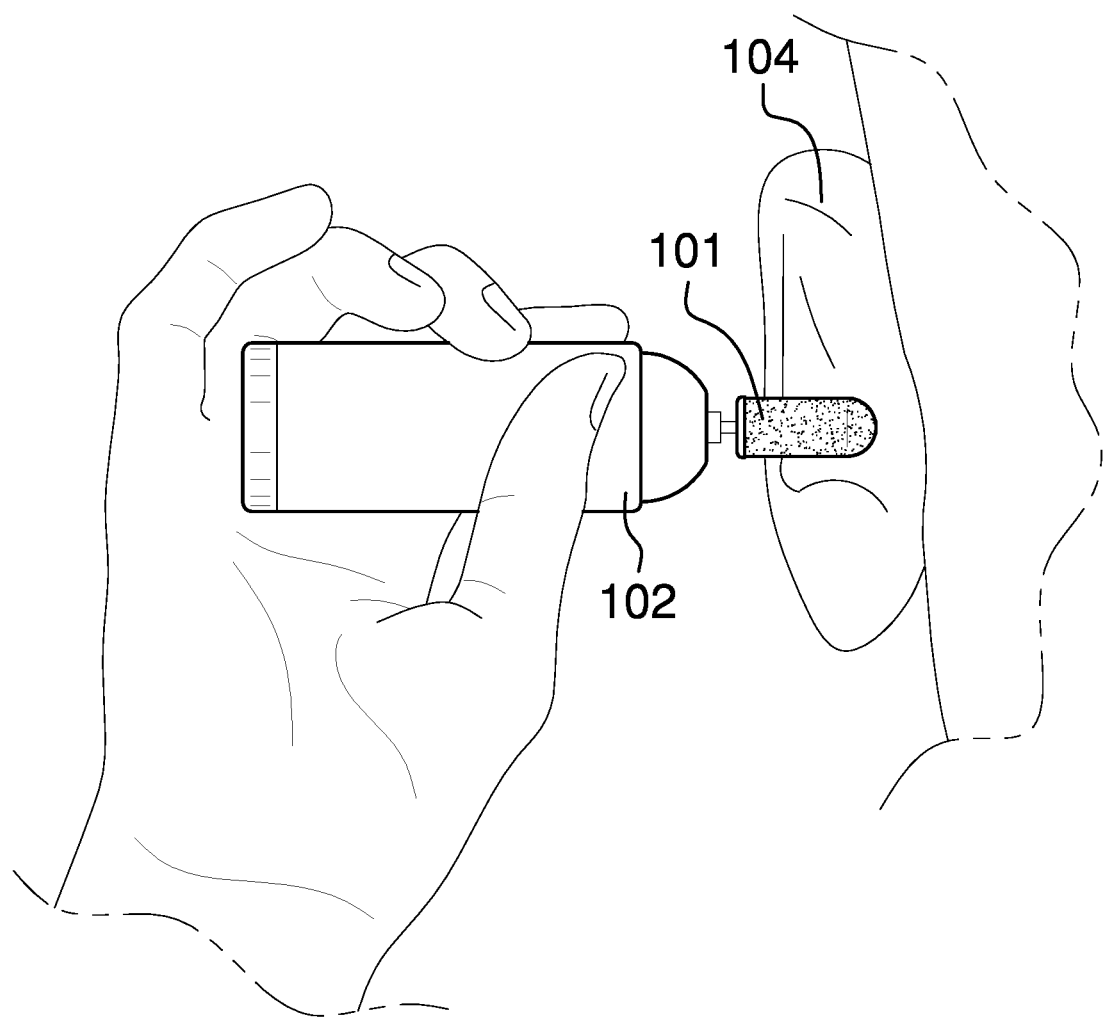
FIG. 3 is an in-use view of an embodiment of the disclosure.

Detailed reference will now be made to one or more potential embodiments of the disclosure, which are illustrated in FIGS. 1 through 3.

The motorized ear-cleaning device 100 (hereinafter invention) is a tool. The invention 100 is a therapeutic device. The invention 100 is adapted for use with the ear 104 of a patient. The invention 100 cleans the ear 104. The invention 100 comprises a working element 101, a handle structure 102, and drive circuit 103. The working element 101 attaches to the handle structure 102. The drive circuit 103 mounts in the drive structure. The drive circuit 103 rotates the working element 101. The rotation of the working element 101 rubs against the ear 104. The working element 101 generates a friction used to clean the ear 104.

The ear 104 is a sensory organ of the patient. The ear 104 detects acoustic energy waves that are propagated through the air.

The working element 101 is the element of the tool formed by the invention 100 that physically cleans the ear 104. The working element 101 is a rotating structure. The rotation of the working element 101 generates a friction that is used to clean the ear 104. The working element 101 physically attaches to the drive circuit 103. The drive circuit 103 provides the motive forces necessary to rotate the working element 101. The working element 101 mounts on the handle structure 102 such that the working element 101 is accessible from the exterior of the handle structure 102. The working element 101 comprises an ear 104 piece 111, an ear 104 pad 112, and a latch structure 113.

The ear 104 piece 111 is a mechanical structure. The ear 104 piece 111 is a fastening device. The ear 104 piece 111 secures the ear 104 pad 112 to the drive circuit 103. The ear 104 piece 111 permanently attaches to the drive circuit 103.

The ear 104 pad 112 removably attaches to the ear 104 piece 111. The ear 104 piece 111 attaches to the drive circuit 103 such that the rotation of the drive circuit 103 rotates both the ear 104 piece 111 and the ear 104 pad 112. The ear 104 pad 112 is an elastic structure. The ear 104 pad 112 is a foam structure. The ear 104 pad 112 removably attaches to the ear 104 piece 111. The ear 104 pad 112 attaches to the ear 104 piece 111 such that the rotation of the ear 104 piece 111 rotates the ear 104 pad 112. The ear 104 pad 112 is placed against the ear 104 such that the rotation of the ear 104 pad 112 against the ear 104 generates a friction used to clean the ear 104.

The latch structure 113 is a fastening device. The latch structure 113 mounts on the ear 104 piece 111. The latch structure 113 removably attaches the ear 104 pad 112 to the ear 104 piece 111. The latch structure 113 secures the ear 104 pad 112 to the ear 104 piece 111 when the ear 104 piece 111 inserts into the ear 104 pad 112. The latch structure 113 further comprises a release linkage 114. The release linkage 114 is a mechanical linkage that is formed in the latch structure 113. The actuation of the release linkage 114 releases the latch structure 113 such that the ear 104 pad 112 can be removed from the ear 104 piece 111.

The handle structure 102 is a grip. The handle structure 102 is used to carry, manipulate, and control the invention 100. The handle structure 102 is a hollow structure. The handle structure 102 contains the drive circuit 103. The handle structure 102 has a roughly tapered prism shape. The handle structure 102 is a rigid structure. The handle structure 102 contains the drive circuit 103. The handle structure 102 is formed with all apertures and form factors necessary to allow the handle structure 102 to accommodate the use and operation of the drive circuit 103. Methods to form a handle structure 102 suitable for the purposes described in this disclosure are well-known and documented in the mechanical arts. The handle structure 102 comprises a shell 121 and a lid 122.

The shell 121 is a tapered prism structure. The shell 121 is a hollow structure. The shell 121 has a pan shape. The shell 121 is a rigid structure. The shell 121 contains the drive circuit 103. The shell 121 is formed with all apertures and form factors necessary to allow the shell 121 to accommodate the use and operation of the drive circuit 103. Methods to form a shell 121 suitable for the purposes described in this disclosure are well-known and documented in the mechanical arts.

The lid 122 is a disk-shaped structure. The lid 122 encloses the open congruent end of the pan structure of the shell 121. The lid 122 attaches to the shell 121 using a threaded connection.

The drive circuit 103 is an electric circuit. The drive circuit 103 converts electric energy into rotational mechanical energy. The drive circuit 103 mechanically attaches to the working element 101. The rotation of the drive circuit 103 rotates the working element 101 during the ear 104 cleaning process. The drive circuit 103 comprises an electric motor 131, a master switch 132, and a battery 133. The electric motor 131, the master switch 132, and the battery 133 are electrically connected.

The electric motor 131 is an electrically powered device. The electric motor 131 is defined elsewhere in this disclosure. The electric motor 131 converts electric energy received from the battery 133 into the rotational energy used to rotate the ear 104 piece 111 and the ear 104 pad 112 of the working element 101. The electric motor 131 further comprises a drive shaft 134. The electric motor 131 rotates the drive shaft 134. The drive shaft 134 attaches to the electric motor 131 such that the axis of rotation of the drive shaft 134 aligns with the center axis of the drive shaft 134. The drive shaft 134 attaches to the drive shaft 134 such that the axis of rotation of the drive shaft 134 aligns with the axis of rotation of the electric motor 131. The drive shaft 134 is a prism-shaped structure. The drive shaft 134 is a rigid structure. The ear 104 piece 111 attaches to the end of the drive shaft 134 that is distal from the electric motor 131. The electric motor 131 rotates the drive shaft 134 such that the rotation of the drive shaft 134 rotates the ear 104 piece 111 and the ear 104 pad 112.

The master switch 132 is a maintained switch. The switch and the maintained switch are defined elsewhere in this disclosure. The master switch 132 controls the flow of electric energy from the battery 133 into the electric motor 131. The master switch 132 controls the operation of the electric motor 131. The battery 133 is an electrochemical device. The battery 133 stores chemical potential energy. The battery 133 converts chemical potential energy into electric energy used to power the electric motor 131. The battery 133 inserts into and is removed from the handle structure 102 through the open congruent end of the pan structure of the shell 121.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Battery: As used in this disclosure, a battery is a chemical device consisting of one or more cells, in which chemical energy is converted into electricity and used as a source of power. Batteries are commonly defined with a positive terminal and a negative terminal.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Center of Rotation: As used in this disclosure, the center of rotation is the point of a rotating plane that does not move with the rotation of the plane. A line within a rotating three-dimensional object that does not move with the rotation of the object is also referred to as an axis of rotation.

Clean: As used in this disclosure, the term clean refers to an object without dirt, unwanted markings, or undesirable pathogens. When referring to a surface, the term clean can also refer to removing unwanted objects from the surface. The term cleaning refers to the action of making an object clean.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Nature: As used in this disclosure, an elastic nature refers to a flexible structure that returns to its relaxed shape after the flexible structure has been deformed.

Electric Motor: In this disclosure, an electric motor is a machine that converts electric energy into rotational mechanical energy. An electric motor typically comprises a stator and a rotor. The stator is a stationary hollow cylindrical structure that forms a magnetic field. The rotor is a magnetically active rotating cylindrical structure that is coaxially mounted in the stator. The magnetic interactions between the rotor and the stator physically causes the rotor to rotate within the stator thereby generating rotational mechanical energy. This disclosure assumes that the power source is an externally provided source of DC electrical power. The use of DC power is not critical and AC power can be used by exchanging the DC electric motor with an AC motor that has a reversible starter winding.

Foam: As used in this disclosure, foam is a mass of gas filled spaces, commonly referred to as bubbles, which can be formed: 1) on or in a liquid or gel; or, 2) in a solid material.

Form Factor: As used in this disclosure, the term form factor refers to the size and shape of an object.

Friction: As used in this disclosure, friction refers to a force that occurs between two objects that are in relative motion while in contact with each other. The force resists the relative motion of the two objects. More technically, friction refers to an exchange of energy between two objects that are in contact with each other that converts the energy of a directed relative motion between the two objects into randomly directed motions of the molecules that form both objects.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Grip: As used in this disclosure, a grip is an accommodation formed on or within an object that allows the object to be grasped or manipulated by a hand.

Handle: As used in this disclosure, a handle is an object by which a tool, object, or door is held or manipulated with the hand.

Housing: As used in this disclosure, a housing is a rigid structure that encloses and protects one or more devices.

Inelastic Nature: As used in this disclosure, an inelastic nature refers to a flexible structure that maintains its new shape after the flexible structure has been deformed.

Latch: As used in this disclosure, a latch is a fastening or locking mechanism. The use of the term latch does not necessarily but often implies the insertion of an object into a notch or cavity.

Maintained Switch: A used in this disclosure, a maintained switch is a switch that maintains the position that was set in the most recent switch actuation. A maintained switch works in an opposite manner to a momentary switch.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to the longest edge of a rectangular structure.

Mechanical Linkage: As used in this disclosure, a mechanical linkage is an interconnected arrangement of components that are used to manage the transfer of a movement or a force. A mechanical linkage is often referred to as a linkage.

Motor: As used in this disclosure, a motor refers to the method of transferring energy from an external power source into rotational mechanical energy.

Negative Space: As used in this disclosure, negative space is a method of defining an object through the use of open or empty space as the definition of the object itself, or, through the use of open or empty space to describe the boundaries of an object.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan is are open.

Patient: As used in this disclosure, a patient is a person who is designated to receive a medical treatment, therapy or service. The term patient may be extended to an animal when used within the context of the animal receiving veterinary treatment or services.

Perimeter: As used in this disclosure, a perimeter is one or more curved or straight lines that bounds an enclosed area on a plane or surface. The perimeter of a circle is commonly referred to as a circumference.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed Shape: As used in this disclosure, a structure is considered to be in its relaxed state when no shear, strain, or torsional forces are being applied to the structure.

Rotation: As used in this disclosure, rotation refers to the cyclic movement of an object around a fixed point or fixed axis. The verb of rotation is to rotate.

Roughly: As used in this disclosure, roughly refers to a comparison between two objects. Roughly means that the difference between one or more parameters of the two compared objects are not significantly different.

Rub: As used in this disclosure, to rub is a verb that means to slide a first object against a second object such that friction is generated between the two objects.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Taper: As used in this disclosure, a taper is a continuous and typically, but not necessarily gradual, change in the span of the length of a structure in the direction parallel a direction selected from the group selected from the major axis and the minor axis of the structure. The change in the span of the length occurs as an apparent function of the measurement position along the unselected axis of the object.

Tapered Prism Structure: As used in this disclosure, a tapered prism structure is a modified prism structure that is formed such that the first congruent end of the modified prism structure is geometrically similar to, but not geometrically identical to the second congruent end of the modified prism. The span of length of a radial line from the center axis to the lateral face of the modified prism structure will vary as a function of its position along the center axis.

Therapeutic: As used in this disclosure, therapeutic is an adjective that refers to a medical, ameliorative, or hygienic substance, process, procedure, or device.

Tool: As used in this disclosure, a tool is a device, an apparatus, or an instrument that is used to carry out an activity, operation, or procedure.

Working Element: As used in this disclosure, the working element of a tool is the physical element on the tool that performs the actual activity, operation, or procedure the tool is designed to perform. For example, the cutting edge of a blade is the working element of a knife.

With respect to the above description, it is to be realized that the optimum dimensional relationship for the various components of the invention described above and in FIGS. 1 through 3 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A motorized ear-cleaning device comprising a working element, a handle structure, and a drive circuit;
   wherein the working element attaches to the handle structure;
   wherein the drive circuit mounts in a drive structure;
   wherein the motorized ear-cleaning device is a tool;
   wherein the motorized ear-cleaning device is a therapeutic device;
   wherein the motorized ear-cleaning device is adapted for use with the ear of a patient;
   wherein the motorized ear-cleaning device is adapted to clean the ear;
   wherein the handle structure comprises a shell and a lid;
   wherein the lid attaches to the shell;
   wherein the shell is a hollow structure;
   wherein the shell has a pan shape;
   wherein the shell is a rigid structure;
   wherein the shell contains the drive circuit;
   wherein the lid is a disk-shaped structure;
   wherein the lid encloses an open congruent end of the pan shape of the shell;
   wherein the lid attaches to the shell using a threaded connection;
   wherein the drive circuit rotates the working element;
   wherein the rotation of the working element is adapted to rub against the ear;
   wherein the working element generates a friction used to clean the ear;
   wherein the working element is an element of the tool formed by the motorized ear-cleaning device that physically cleans the ear;
   wherein the working element is a rotating structure;

wherein the rotation of the working element generates the friction that is used to clean the ear;
wherein the working element physically attaches to the drive circuit;
wherein the drive circuit provides motive forces necessary to rotate the working element;
wherein the working element mounts on the handle structure such that the working element is accessible from the exterior of the handle structure;
wherein the handle structure is a grip;
wherein the handle structure is used to carry, manipulate, and control the motorized ear-cleaning device;
wherein the handle structure is a hollow structure;
wherein the handle structure contains the drive circuit;
wherein the handle structure is a rigid structure;
wherein the drive circuit is an electric circuit;
wherein the drive circuit converts electric energy into rotational mechanical energy;
wherein the drive circuit mechanically attaches to the working element;
wherein the rotation of the drive circuit rotates the working element during the ear cleaning process;
wherein the working element comprises an ear piece, an ear pad, and a latch structure;
wherein the latch structure secures the ear pad to the ear piece;
wherein the drive circuit comprises an electric motor, a master switch, and a battery;
wherein the electric motor, the master switch, and the battery are electrically connected;
wherein the ear piece is a mechanical structure;
wherein the ear piece is a fastening device;
wherein the ear piece secures the ear pad to the drive circuit;
wherein the ear piece permanently attaches to the drive circuit;
wherein the ear piece attaches to the drive circuit such that the rotation of the drive circuit rotates both the ear piece and the ear pad;
wherein the ear pad is an elastic structure;
wherein the ear pad is a foam structure;
wherein the ear pad removably attaches to the ear piece;
wherein the ear pad attaches to the ear piece such that the rotation of the ear piece rotates the ear pad.

2. The motorized ear-cleaning device according to claim 1 wherein the latch structure is a fastening device;
wherein the latch structure mounts on the ear piece;
wherein the latch structure removably attaches the ear pad to the ear piece;
wherein the latch structure secures the ear pad to the ear piece when the ear piece inserts into the ear pad;
wherein the latch structure further comprises a release linkage;
wherein the release linkage is a mechanical linkage that is formed in the latch structure;
wherein the actuation of the release linkage releases the latch structure such that the ear pad can be removed from the ear piece.

3. The motorized ear-cleaning device according to claim 2 wherein the electric motor is an electrically powered device;
wherein the electric motor converts electric energy received from the battery into the rotational energy used to rotate the ear piece and the ear pad of the working element.

4. The motorized ear-cleaning device according to claim 3 wherein the electric motor further comprises a drive shaft;
wherein the electric motor rotates the drive shaft;
wherein the drive shaft attaches to the electric motor such that the axis of rotation of the drive shaft aligns with the center axis of the drive shaft;
wherein the drive shaft attaches to the electric motor such that the axis of rotation of the drive shaft aligns with the axis of rotation of the electric motor;
wherein the drive shaft is a rigid structure;
wherein the ear piece attaches to the end of the drive shaft that is distal from the electric motor.

5. The motorized ear-cleaning device according to claim 4 wherein the master switch is a maintained switch;
wherein the master switch controls the flow of electric energy from the battery into the electric motor;
wherein the master switch controls the operation of the electric motor;
wherein the battery is an electrochemical device;
wherein the battery converts chemical potential energy into electric energy used to power the electric motor.

* * * * *